United States Patent [19]
White et al.

[11] Patent Number: 5,110,546
[45] Date of Patent: May 5, 1992

[54] METHOD FOR LOCATING METALLIC NITRIDE INCLUSIONS IN METALLIC ALLOY INGOTS

[75] Inventors: Jack C. White, Albany; Davis E. Traut, Corvallis; Laurance L. Oden, Albany; Roman A. Schmitt, Corvallis, all of Oreg.

[73] Assignee: The United States of America as represented by the Secretary of the Interior, Washington, D.C.

[21] Appl. No.: 696,805

[22] Filed: May 7, 1991

[51] Int. Cl.⁵ .............................................. C22C 1/00
[52] U.S. Cl. ................................................... 420/590
[58] Field of Search ................. 420/590; 148/14, 247; 423/353

[56] References Cited

U.S. PATENT DOCUMENTS 3,241,919  3/1966  O'Connor .......................... 148/14
3,622,309  10/1968  Hill .................................. 420/590

Primary Examiner—Peter D. Rosenberg
Attorney, Agent, or Firm—E. Philip Koltos

[57] ABSTRACT

A method of determining the location and history of metallic nitride and/or oxynitride inclusions in metallic melts. The method includes the steps of labeling metallic nitride and/or oxynitride inclusions by making a coreduced metallic-hafnium sponge from a mixture of hafnium chloride and the chloride of a metal, reducing the mixed chlorides with magnesium, nitriding the hafnium-labeled metallic-hafnium sponge, and seeding the sponge to be melted with hafnium-labeled nitride inclusions. The ingots are neutron activated and the hafnium is located by radiometric means. Hafnium possesses exactly the proper metallurgical and radiochemical properties for this use.

12 Claims, No Drawings

METHOD FOR LOCATING METALLIC NITRIDE INCLUSIONS IN METALLIC ALLOY INGOTS

Technical Field

This invention relates to a method of locating metallic nitride and/or oxynitride inclusions, and more particularly to a method for determining which melt process is most effective in dissolving harmful nitride or oxynitride inclusions in metals such as titanium, zirconium, and their alloys.

BACKGROUND ART

High speed rotating aircraft parts require high-strength metals such as titanium. Titanium nitride or oxynitride inclusions in titanium and titanium alloy parts lower strength, sometimes with disastrous results. The titanium nitride-oxynitride inclusions are also known in the industry as Type 1 hard alpha inclusions. Investigators have searched for the best means during various melting methods, for dissolving titanium nitride inclusions that may cause failure of high-speed, rotating, titanium alloy parts in jet engines. No accurate or quantitative means is presently available to determine the dissolution history of such inclusions. A large volume of work has been done on titanium nitride inclusions. While large, well-defined inclusions can be found by ultrasonic or radiographic (X-ray) means, there is presently no means of determining these inclusions if they are metallurgically continuous.

Those concerned with these and other problems recognize the need for an improved method for locating metallic nitride inclusions in metallic alloy ingots.

DISCLOSURE OF THE INVENTION

The present invention provides a method of determining the location and history of metallic nitride and/or oxynitride inclusions in metallic melts. The method includes the steps of labeling metallic nitride and/or oxynitride inclusions by making a coreduced metallic-hafnium sponge from a mixture of hafnium chloride and the chloride of a metal, reducing the mixed chlorides with magnesium, nitriding the hafnium-labeled metallic-hafnium sponge, and seeding the sponge to be melted with hafnium-labeled nitride pieces. The ingots are neutron activated and the hafnium is located by radiometric means. Hafnium possesses exactly the proper metallurgical and radiochemical properties for this use.

The magnesium reduction of chlorides is only one technique for the production of metallic hafnium alloys for use as tracers. Others include melting metals together as in a button furnace, use of metallic-hafnium powder compacts, coreduction using a different reducing metal such as Na or K, or coreduction by electrolytic means from fused salts or non-aqueous solvents.

An object of the present invention is the provision of an improved method for locating metallic nitride inclusions in metallic alloy ingots.

Another object is to provide a method of locating inclusions that provides information that assists in choosing the best process for eliminating the nitride inclusions.

These and other attributes of the invention will become more clear upon a thorough study of the following description of the best mode for carrying out the invention, particularly when reviewed in conjunction with the examples.

BEST MODE FOR CARRYING OUT THE INVENTION

The following examples are illustrative of the best mode for carrying out the invention. They are obviously not to be construed as limitative of the invention since various other embodiments can readily be evolved in view of the teachings provided herein.

A need has existed from the beginnings of the titanium and zirconium industry for a means to determine quantitatively the dissolution or partial dissolution of nitride and/or oxynitride inclusions in ingots or billets. If a means were found for tracking nitride or oxynitride inclusions through the melting and fabrication processes, then the best processes for minimizing such inclusions could be identified and used. This invention offers such a means of tracking nitride or oxynitride inclusions as an analytical technique for determining the best processing steps.

This invention is the result of a fortuitous combination of the properties of the metal hafnium as applied to the specific problem mentioned above. Hafnium in low concentration forms a solid solution with titanium or zirconium. The binary phase diagrams show that no hafnium-titanium or hafnium-zirconium separation occurs upon crystallization from the melt, a desirable property for this use. Furthermore, titanium nitride, zirconium nitride, and hafnium nitride have a similar solid solution, and their free energies of formation are similar, also desirable properties. The nuclear properties of hafnium are a third factor essential to this invention. Hafnium has a large thermal neutron capture cross section, and $^{181}$hafnium emits two gamma rays of intermediate energy that can be used to detect hafnium-labeled inclusions at depth and a 0.4 MeV beta that can be used for autoradiography. The $^{181}$hafnium isotope also has a half life of about 42 days, ideal for this application.

Hafnium labeling of titanium nitride or zirconium nitride inclusions may be done by a number of means previously listed, but the preferred embodiment is described in the following steps:

1. Coreduction of $TiCl_4$—$HfCl_4$ or $ZrCl_4$—$HfCl_4$ containing only a few percent of hafnium to form a titanium-hafnium or zirconium-hafnium alloy sponge.
2. Reaction of hafnium-labeled sponge with air or nitrogen gas to produce hafnium-labeled titanium oxynitride or nitride or zirconium oxynitride or nitride sponge particles.

In dealing with zirconium alloys which contain a high background level of hafnium which would also activate on exposure to neutrons, the neutron activation must be done to the nitride or oxynitride sponge seeds prior to melting into the ingots. Therefore, for zirconium, this step fits between steps 2 and 3 and is equivalent to inserting step 6 (of the titanium route) between step 2 and 3, but is applicable to zirconium only.

3. Seeding of titanium or zirconium sponge with the hafnium-labeled nitride pieces to produce labeled sponge compacts to be used in fabricating consumable bars or electrodes for melting by various secondary melting methods such as vacuum arc remelting.
4. Melting the bars or electrodes so produced by the various melting methods to produce consolidated ingots.

5. Cross sectioning the ingots, so produced, after one or more melting steps and machining or polishing the surfaces.
6. Neutron activation with thermalized neutrons to activate $^{180}$hafnium$+n\rightarrow{}^{181}$hafnium. Allowing short-lived isotopes to die away and counting the gamma radiation to detect hidden inclusions. The emission of two gamma rays at 0.482 and 0.133 MeV energy levels will allow location of the depth of inclusions in the sample by determining the ratio of counts of the two gamma energy levels. Location of inclusions will be by means of slit collimators in lead bricks. A second means of determining accurately the spatial configuration of hafnium-labeled material is by autoradiographic exposures using the 0.408 MeV beta emission. Autoradiographic film will record most of the beta and much less of the gamma, providing essentially a contact print of hafnium distribution of the surface with minimal signal from within the sample.
7. Typically, an activation time of a few hours (10 hours) and an autoradiography time of a few days should produce adequate radiographs. Counting of gamma radiation will be much faster. First, a wide slit will be used (1 cm), and later, a 2-mm slit will be used for finer resolution of position of the inclusions.
8. This examination means can be conducted on both ingots and fabricated parts and will provide an unequivocal identification of the position of labeled inclusions and also of material associated with inclusions that have completely dissolved, even after fabrication.
9. The levels of detection are so sensitive that very small amounts of hafnium are needed, much less than 1% in the alloy ingots for detection. By the above outlined means, the history and spatial distribution of hafnium-labeled titanium nitride or zirconium nitride inclusions may be traced through melting and fabrication. For the first time, a choice of the best melting technology may be made on the basis of accurately determined results.

The advantages of the present invention are that very small inclusions may be found by radiometric counting of gamma rays or by autoradiography with photographic film. Furthermore, the dissolved nitride inclusion materials can be found showing the degree of mixing and dispersion after dissolution. This latter effect cannot be determined by any other known method.

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

We claim:

1. A method of quantitatively determining the dissolution history of metallic nitride inclusions in metallic melts, comprising the steps of:
   preparing a mixture of the halide of a metal and hafnium halide;
   coreducing the mixture to form a metallic-hafnium alloy sponge;
   nitriding or reacting in air the metallic-hafnium alloy sponge to form hafnium-labeled nitride or oxynitride inclusions;
   seeding the metallic sponge to be melted with the hafnium-labeled nitride pieces to form ingots;
   neutron activating the ingots; and
   determining the hafnium location in the ingots by radiometric means.

2. The method of claim 1 wherein said metal forms a solid solution with low concentrations of hafnium.

3. The method of claim 1 wherein said metal does not separate upon crystallization from a melt with hafnium.

4. The method of claim 1 wherein the nitride of said metal has a solid solution similar to hafnium nitride.

5. The method of claim 1 wherein the nitride of said metal has a free energy of formation similar to hafnium nitride.

6. The method of claim 1 wherein said metal is an element of group IV B of the periodic table.

7. The method of claim 1 wherein said metal is selected from a group consisting of titanium and zirconium.

8. The method of claim 1 wherein said metal is zirconium and wherein the hafnium labelled nitrided seeds are neutron activated prior to melting into ingots.

9. The method of claim 7 wherein said mixture includes $TiCl_4$ and $HfCl_4$.

10. The method of claim 7 wherein said mixture includes $ZrCl_4$ and $HfCl_4$.

11. The method of claim 9 wherein said hafnium is present in an amount of less than five percent by weight in the hafnium labeled pieces, and preferably from one to three percent.

12. The method of claim 10 wherein said hafnium is present in an amount of less than five percent by weight in the hafnium labeled pieces, and preferably from one to three percent.

* * * * *